(12) United States Patent
Defossez et al.

(10) Patent No.: US 9,186,484 B2
(45) Date of Patent: Nov. 17, 2015

(54) GUIDEWIRE INSERTION METHODS AND DEVICES

(71) Applicant: DePuy Synthes Products, Inc., Raynham, MA (US)

(72) Inventors: Henri Defossez, Neuchatel (CH); Frank Spratt, Bole, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/141,745

(22) Filed: Dec. 27, 2013

(65) Prior Publication Data

US 2014/0114291 A1    Apr. 24, 2014

Related U.S. Application Data

(63) Continuation of application No. 12/829,062, filed on Jul. 1, 2010, now Pat. No. 8,641,717.

(51) Int. Cl.
*A61F 2/46* (2006.01)
*A61M 25/09* (2006.01)
(Continued)

(52) U.S. Cl.
CPC ...... *A61M 25/09041* (2013.01); *A61B 17/8872* (2013.01); *A61M 29/00* (2013.01);
(Continued)

(58) Field of Classification Search
CPC ........... A61B 17/8872; A61B 17/8897; A61B 2017/22047; A61B 2017/22049; A61B 2017/347; A61B 17/17; A61B 17/86; A61B 17/8861; A61B 5/6851; A61M 25/09041; A61M 2025/09116; A61M 2025/09125; A61M 25/0169
USPC ........................................ 606/86 R; 600/585
See application file for complete search history.

(56) References Cited

U.S. PATENT DOCUMENTS

| 4,341,206 A | 7/1982 | Perrett et al. |
| 4,450,835 A | 5/1984 | Asnis et al. |

(Continued)

FOREIGN PATENT DOCUMENTS

| EP | 0 253 526 A1 | 1/1988 |
| EP | 0 440 371 A1 | 8/1991 |

(Continued)

OTHER PUBLICATIONS

[No Author Listed] A New Angle on Correction. Expedium. DePuy. 2009. 2 pages.

(Continued)

*Primary Examiner* — Anu Ramana
(74) *Attorney, Agent, or Firm* — Nutter McClennen & Fish LLP

(57) ABSTRACT

Various methods and devices for inserting a guidewire into the body are provided. In one embodiment, a guidewire insertion device is provided and includes and outer sheath having an outer surface and an inner lumen extending therethrough, and a dilator having an inner lumen extending therethrough and having a length greater than a length of the outer sheath. A guidewire can be configured to extend through the inner lumen of the dilator such that the guidewire is removably and replaceably disposable within the dilator and coupled thereto. A locking mechanism can be effective to selectively configure the guidewire between a locked position in which the guidewire is stationary relative to the dilator and an unlocked position in which the guidewire is movable relative to the dilator.

18 Claims, 13 Drawing Sheets

(51) Int. Cl.
*A61B 17/88* (2006.01)
*A61M 29/00* (2006.01)
A61B 17/34 (2006.01)
A61B 17/22 (2006.01)

(52) U.S. Cl.
CPC ......... *A61B17/3421* (2013.01); *A61B 17/8897* (2013.01); *A61B 2017/22047* (2013.01); *A61B 2017/22049* (2013.01); *A61B 2017/347* (2013.01)

(56) References Cited

U.S. PATENT DOCUMENTS

| | | | |
|---|---|---|---|
| 4,541,423 A | 9/1985 | Barber | |
| 4,683,896 A | 8/1987 | Herbst et al. | |
| 4,706,659 A | 11/1987 | Matthews et al. | |
| 4,710,075 A | 12/1987 | Davison | |
| 4,751,922 A | 6/1988 | DiPietropolo | |
| 5,045,061 A * | 9/1991 | Seifert et al. | 604/96.01 |
| 5,180,384 A | 1/1993 | Mikhail | |
| 5,354,300 A | 10/1994 | Goble et al. | |
| 5,374,270 A | 12/1994 | McGuire et al. | |
| 5,409,470 A | 4/1995 | McIntyre et al. | |
| 5,423,819 A | 6/1995 | Small et al. | |
| 5,458,604 A | 10/1995 | Schmieding | |
| 5,499,984 A | 3/1996 | Steiner et al. | |
| 5,573,537 A | 11/1996 | Rogozinski | |
| 5,645,545 A | 7/1997 | Bryant | |
| 5,658,289 A | 8/1997 | Boucher et al. | |
| 5,695,513 A | 12/1997 | Johnson et al. | |
| 5,720,749 A | 2/1998 | Rupp | |
| 5,851,189 A | 12/1998 | Forber | |
| 5,879,350 A | 3/1999 | Sherman et al. | |
| 6,019,776 A | 2/2000 | Preissman et al. | |
| 6,053,917 A | 4/2000 | Sherman et al. | |
| 6,056,753 A | 5/2000 | Jackson | |
| 6,113,601 A | 9/2000 | Tatar | |
| 6,280,442 B1 | 8/2001 | Barker et al. | |
| 6,402,757 B1 | 6/2002 | Moore, III et al. | |
| 6,660,004 B2 | 12/2003 | Barker et al. | |
| 6,736,820 B2 | 5/2004 | Biedermann et al. | |
| 6,827,722 B1 | 12/2004 | Schoenefeld | |
| 6,955,678 B2 | 10/2005 | Gabriel et al. | |
| 6,974,460 B2 | 12/2005 | Carbone et al. | |
| 6,981,974 B2 | 1/2006 | Berger | |
| 7,022,122 B2 | 4/2006 | Amrein et al. | |
| 7,087,057 B2 | 8/2006 | Konieczynski et al. | |
| 7,179,261 B2 | 2/2007 | Sicvol et al. | |
| 7,186,255 B2 | 3/2007 | Baynham et al. | |
| 7,207,995 B1 | 4/2007 | Vandewalle | |
| 7,322,981 B2 | 1/2008 | Jackson | |
| 7,325,470 B2 | 2/2008 | Kay et al. | |
| 7,338,494 B2 | 3/2008 | Ryan | |
| 7,445,627 B2 | 11/2008 | Hawkes et al. | |
| 7,488,323 B2 | 2/2009 | Bacastow et al. | |
| 7,604,643 B2 | 10/2009 | Ciccone et al. | |
| 7,615,068 B2 | 11/2009 | Timm et al. | |
| 7,670,316 B2 | 3/2010 | Windheuser et al. | |
| 7,686,833 B1 | 3/2010 | Muhanna et al. | |
| 7,727,261 B2 | 6/2010 | Barker et al. | |
| 7,766,946 B2 | 8/2010 | Bailly | |
| 7,785,354 B2 | 8/2010 | Biedermann et al. | |
| 7,789,900 B2 | 9/2010 | Levy et al. | |
| 7,892,207 B2 | 2/2011 | Simonton et al. | |
| 7,938,836 B2 | 5/2011 | Ainsworth et al. | |
| 8,007,522 B2 | 8/2011 | Hutchinson | |
| 8,092,494 B2 | 1/2012 | Butler et al. | |
| 8,100,946 B2 | 1/2012 | Strausbaugh et al. | |
| 8,162,989 B2 | 4/2012 | Khalili | |
| 8,167,910 B2 | 5/2012 | Nilsson | |
| 8,167,912 B2 | 5/2012 | Jacofsky et al. | |
| 8,192,466 B2 | 6/2012 | Yue et al. | |
| 8,197,517 B1 | 6/2012 | Lab et al. | |
| 8,197,518 B2 | 6/2012 | Hammill, Sr. et al. | |
| 8,216,243 B2 | 7/2012 | Yevmenenko et al. | |
| 8,221,472 B2 | 7/2012 | Peterson et al. | |
| 8,236,006 B2 | 8/2012 | Hamada | |
| 8,273,112 B2 | 9/2012 | Garamszegi et al. | |
| 8,282,651 B2 | 10/2012 | Ciccone et al. | |
| 8,287,576 B2 | 10/2012 | Barrus | |
| 8,298,274 B2 | 10/2012 | Barker, Jr. et al. | |
| 8,303,601 B2 | 11/2012 | Bandeira et al. | |
| 8,308,782 B2 | 11/2012 | Jackson | |
| 8,313,515 B2 | 11/2012 | Brennan et al. | |
| 8,313,516 B2 | 11/2012 | Konieczynski et al. | |
| 8,337,530 B2 | 12/2012 | Hestad et al. | |
| 8,372,076 B2 | 2/2013 | Simonton et al. | |
| 8,394,108 B2 | 3/2013 | McLean et al. | |
| 8,409,260 B2 | 4/2013 | Biedermann et al. | |
| 2003/0013936 A1 | 1/2003 | Jackson | |
| 2003/0055426 A1 | 3/2003 | Carbone et al. | |
| 2003/0055431 A1 | 3/2003 | Brannon | |
| 2005/0049592 A1 | 3/2005 | Keith et al. | |
| 2005/0216027 A1 | 9/2005 | Suh et al. | |
| 2007/0016219 A1 | 1/2007 | Levine | |
| 2008/0119852 A1 | 5/2008 | Dalton et al. | |
| 2008/0147128 A1 | 6/2008 | Fritzinger | |
| 2008/0177335 A1 | 7/2008 | Melkent | |
| 2008/0200956 A1 | 8/2008 | Beckwith et al. | |
| 2008/0269809 A1 | 10/2008 | Garamszegi | |
| 2009/0018591 A1 | 1/2009 | Hawkes et al. | |
| 2009/0198280 A1 | 8/2009 | Spratt et al. | |
| 2009/0275994 A1 | 11/2009 | Phan et al. | |
| 2009/0287261 A1 | 11/2009 | Jackson | |
| 2010/0114174 A1 | 5/2010 | Jones et al. | |
| 2010/0198270 A1 | 8/2010 | Barker et al. | |
| 2010/0198272 A1 | 8/2010 | Keyer et al. | |
| 2010/0241124 A1 | 9/2010 | Housman et al. | |
| 2011/0054537 A1 | 3/2011 | Miller et al. | |
| 2011/0245876 A1 | 10/2011 | Brumfield | |
| 2011/0282399 A1 | 11/2011 | Jackson | |
| 2011/0288599 A1 | 11/2011 | Michielli et al. | |
| 2011/0295321 A1 | 12/2011 | Hutchinson | |
| 2012/0004665 A1 | 1/2012 | Defossez et al. | |
| 2012/0010661 A1 | 1/2012 | Farris et al. | |
| 2012/0035670 A1 | 2/2012 | Jackson et al. | |
| 2012/0089194 A1 | 4/2012 | Strausbaugh et al. | |
| 2012/0197313 A1 | 8/2012 | Cowan | |
| 2012/0253404 A1 | 10/2012 | Timm et al. | |
| 2012/0303070 A1 | 11/2012 | Jackson | |
| 2012/0310290 A1 | 12/2012 | Jackson | |
| 2012/0316605 A1 | 12/2012 | Palagi | |
| 2012/0330364 A1 | 12/2012 | Jacofsky et al. | |
| 2013/0012954 A1 | 1/2013 | Paroth et al. | |
| 2013/0053901 A1 | 2/2013 | Cormier et al. | |
| 2013/0096618 A1 | 4/2013 | Chandanson et al. | |

FOREIGN PATENT DOCUMENTS

| | | |
|---|---|---|
| EP | 1 570 794 A1 | 9/2005 |
| EP | 2 272 451 A1 | 1/2011 |
| WO | 03/022165 A1 | 3/2003 |
| WO | 2008/024937 A2 | 2/2008 |
| WO | 2011/127065 A1 | 10/2011 |
| WO | 2012/024665 A2 | 2/2012 |
| WO | 2013/028851 A1 | 2/2013 |

OTHER PUBLICATIONS

[No Author Listed] DePuy Spine Pedicle Probe with Tap—Sold or offered for sale in 2008 (1 page).

[No Author Listed] Straight Talk with Expedium. Expedium. 10 pages. Jul. 2007.

[No Author Listed] Surgical Technique Guide and Ordering Information. Expedium. DePuy Spine Inc. Sep. 2011. 24 pages.

[No Author Listed] Value Analysis Brief—Expedium Favored Angle Screw. DePuy Synthes Spine. Aug. 2012. 4 pages.

[No Author Listed] Viper 2 MIS Spine System. System Guide. DePuy Spine Inc. Sep. 2011. 60 pages.

\* cited by examiner

GUIDEWIRE INSERTION METHODS AND DEVICES

FIELD

This application is a continuation of U.S. Ser. No. 12/829,062 filed on Jul. 1, 2010, and entitled "Guidewire Insertion Methods and Devices" which is incorporated by reference herein.

BACKGROUND

Dilators are widely used in medical procedures to gain access to body cavities by dilating tissue and formed a working channel therethrough for the insertion of instruments and other materials. The use of dilators and access ports has become more common as they provide minimally invasive techniques for establishing a portal for a number of procedures.

In a typical procedure, a guidewire is inserted into the body, and then a dilator is pushed through the tissue over the guidewire to dilate the tissue. The dilator can then be used as a working channel through the tissue for accessing a surgical site. Various other types of devices can then be inserted through the dilator, including needles to anchor to bone. One such device is a Jamshidi needle, that is a long, hollow needle having a cutting edge on one end and a handle and syringe attachment on the other end to remove a sample of tissue from bone marrow. While effective, there can be many disadvantages to these types of techniques. Specifically, there is a larger number of steps required to access the body, and ultimately bone, with various devices being inserted through tissue and into the body separately.

Accordingly, there is a need for improved methods and devices for providing access into a body cavity, and in particular for inserting a guidewire into the body and/or into bone.

SUMMARY

Methods and devices are provided for inserting a guidewire into the body. In one exemplary embodiment, a guidewire insertion device is provided and it includes an outer sheath having an outer surface and an inner lumen extending therethrough, and a dilator having an inner lumen extending therethrough and having a length greater than a length of the outer sheath. The dilator can be configured to be removably disposable within the outer sheath such that a distal portion of the dilator is configured to extend from a distal end of the outer sheath and a proximal handle portion of the dilator is configured to extend from a proximal end of the outer sheath when the dilator is disposed in the outer sheath. The distal portion of the dilator has an outer diameter that increases proximally along a length of the distal portion. A guidewire can be configured to extend through the inner lumen of the dilator such that the guidewire is removably and replaceably disposable within the dilator and coupled thereto. A locking mechanism can be effective to selectively configure the guidewire between a locked position in which the guidewire is stationary relative to the dilator and an unlocked position in which the guidewire is movable relative to the dilator.

In one embodiment, the guidewire can be configured to extend from a distal end of the dilator. For example, the guidewire extends from the distal end of the dilator between a distance of 1 mm to 250 mm. The guidewire can also include a variety of other features. In one embodiment, the guidewire includes bone-engaging features formed on a distal portion thereof. For example, the bone-engaging features can be in the form of threads formed on the distal portion of the guidewire.

The locking mechanism can have a variety of configurations, but in one exemplary embodiment, the locking mechanism is slidably disposed over the guidewire and is configured to removably couple to the dilator. The locking mechanism can be in the form of a locking bolt having a lumen extending therethrough such that the bolt is configured to slide over the guidewire. The locking bolt can have threads formed on a distal end thereof such that the locking bolt can mate with corresponding threads formed in a proximal end of the handle of the dilator to cause the distal end of the locking bolt to compress and lock the guidewire relative to the dilator in the locked position. In one embodiment, the handle includes a bore formed in a proximal end thereof that includes the corresponding threads, and the bore is tapered such that the bore causes the distal end of the locking bolt to compress as the locking bolt is mated with the corresponding threads in the bore. To allow the locking bolt to compress, the distal end of the locking bolt can include a compressible opening formed therein and having the threads formed thereon such that the compressible opening can be compressed in the locked position to lock the guidewire relative to the dilator. For example, the distal end of the locking bolt can include at least one slit formed therethrough and configured to allow the locking bolt to compress to lock the guidewire relative to the dilator.

In another exemplary embodiment, the locking mechanism can be pivotally coupled to the dilator such that pivotal movement of the locking mechanism is configured to apply force to the guidewire to lock the guidewire relative to the dilator. The locking mechanism is in the form of an elongate member with a distal end pivotally coupled to the dilator in an opening formed in a sidewall of the dilator such that the distal end of the elongate member is configured to be positioned against the guidewire in the locked positioned and position separated from the guidewire in the unlocked position. In yet another exemplary embodiment, the locking mechanism includes a biasing element disposed around a portion of the dilator and configured to bias locking arms into engagement with the guidewire to position the guidewire in the locked position.

Methods for inserting a guidewire into bone are also provided, and in one embodiment the method can include advancing a dilator through tissue to dilate the tissue and form a working channel therethrough. The dilator can be removably disposed within an outer sheath and having a guidewire extending through an inner lumen of the dilator such that the guidewire protrudes from a distal end of the dilator and the guidewire is locked and stationary relative to the dilator. The method also includes unlocking the guidewire from the dilator such that the guidewire is movable relative to the dilator. For example, unlocking the guidewire can include disengaging a locking mechanism at a proximal end of the dilator such that the locking mechanism decouples the guidewire from to the dilator. The method further includes removing the dilator from the outer sheath while maintaining the guidewire and outer sheath in position to provide a working channel through the outer sheath.

The method can further include anchoring the guidewire to bone. For example, a force can be applied to a proximal end of the guidewire when a distal end of the guidewire is adjacent to bone to anchor the guidewire to bone.

BRIEF DESCRIPTION OF THE DRAWINGS

The invention will be more fully understood from the following detailed description taken in conjunction with the accompanying drawings, in which.

DETAILED DESCRIPTION

Figure 1:
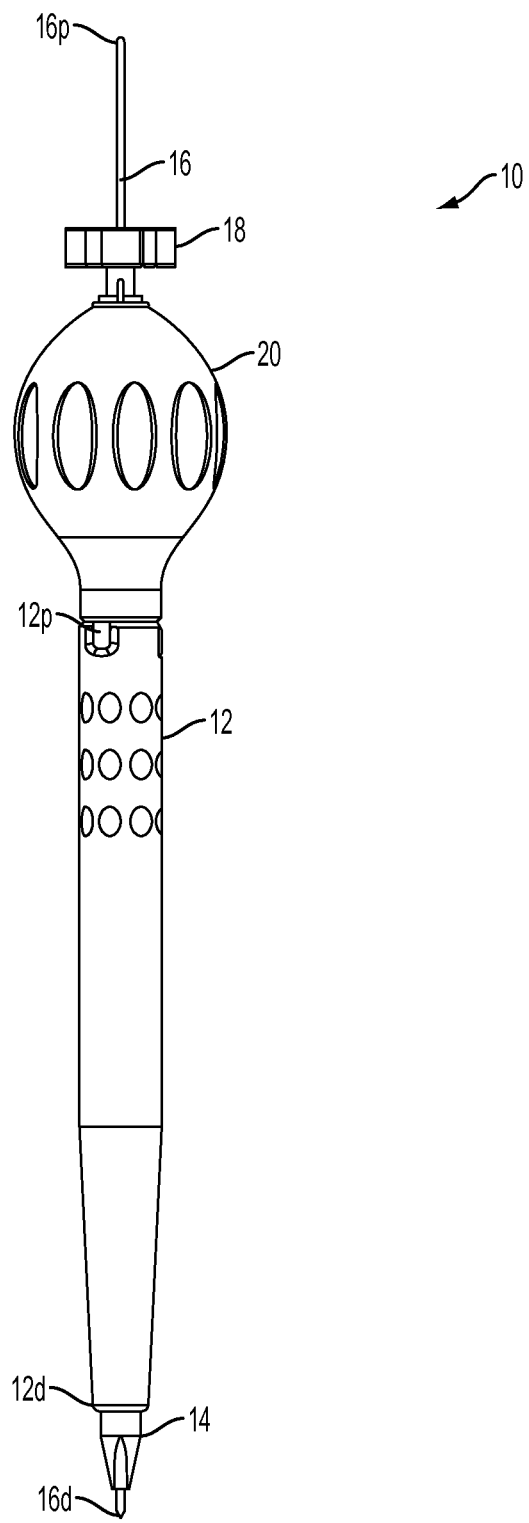
FIG. 1 is a side view of an exemplary embodiment of guidewire insertion device showing a locking mechanism in a locked position such that a guidewire is locked relative to a dilator disposed within an outer sheath.
Figure 2:
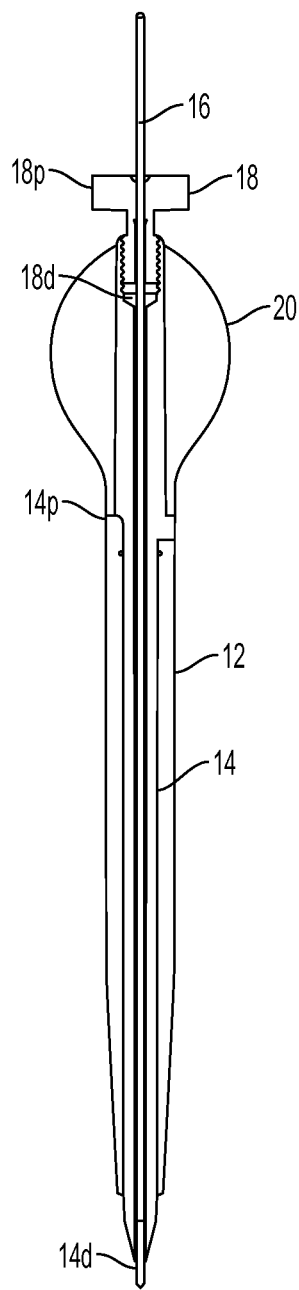
FIG. 2 is a cross-sectional side view of the guidewire insertion device of FIG. 1.
Figure 3:
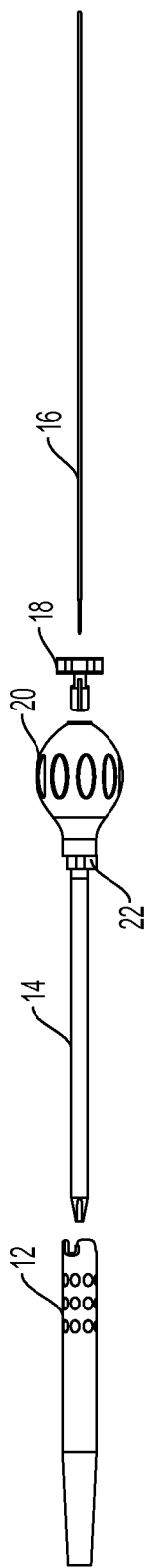
FIG. 3 is an exploded view of the guidewire insertion device of FIG. 1.
Figure 4:
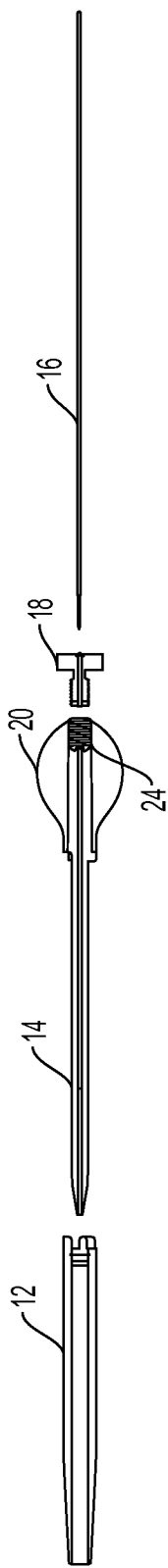
FIG. 4 is a cross-sectional exploded view of the guidewire insertion device of FIG. 1.
Figure 5:
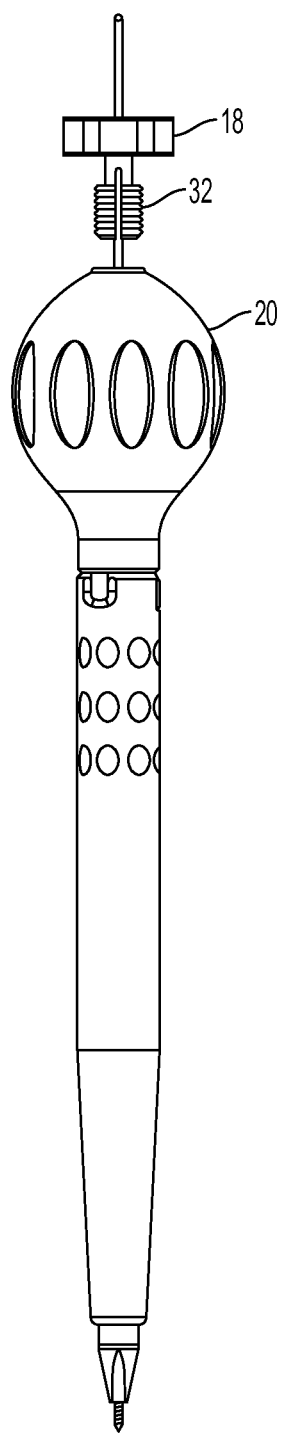
FIG. 5 is a side view of the guidewire insertion device of FIG. 1 showing the locking mechanism in an unlocked position.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various methods and devices are provided for inserting a guidewire into the body, and in particular into bone. In general, a guidewire insertion device is provided that is adapted to insert a guidewire into the body, while also forming a working channel through tissue. The use of the device is particularly advantageous as it allows for the dilation of tissue and the formation of the working channel while inserting the guidewire, thus combining these steps in the procedure for providing access to the body.

FIGS. 1-8 illustrate one exemplary embodiment of a guidewire insertion device 10 that includes an outer sheath 12 having an inner lumen extending therethrough, and a dilator 14 that is configured to extend through the inner lumen of the outer sheath 12 and to dilate tissue to form a working channel to provide access into the body. A guidewire 16 is configured to extend through the dilator 14 such that the guidewire 16 can be removably disposed therein and mated thereto using a locking mechanism 18. The locking mechanism 18 is configured to selectively lock the guidewire 16 relative to the dilator 14 such that the guidewire 16 is stationary relative to the dilator 14 in a locked position, and movable relative to the dilator 14 in an unlocked position. This allows the guidewire 14 to be locked relative to the dilator 14 during insertion of the guidewire insertion device 10 into the body, and movable relative to the dilator 14 after insertion of the guidewire insertion device 10 into the body to allow the dilator 14 to be removed and leaving the guidewire 16, and optionally the outer sheath 12, in place in the body.

The outer sheath 12 can have a variety of configurations, but in the illustrated embodiment the outer sheath 12 is in the form of an elongate shaft having proximal and distal ends 12p, 12d with the inner lumen extending therethrough. The particular length of the outer sheath 12 can vary, but the outer sheath 12 typically has a length such that the outer sheath 12 can extend through the tissue to form a working channel that provides access into a body cavity with a distal end 12d of the outer sheath 12 extending into the body cavity and the proximal end 12p of the outer sheath 12 remaining outside the body. The diameter of the outer sheath 12 can also vary, but typically the outer sheath 12 has a diameter such that the inner lumen of the outer sheath 12 is configured to receive a variety of instruments and/or other devices therethrough, including but not limited to the dilator 14 and the guidewire 16. For example, the outer sheath 12 can have an outer diameter of approximately 10 mm to 15 mm.

The dilator 14 can also have a variety of configurations. In the illustrated embodiment, the dilator 14 is in the form of an elongate shaft having proximal and distal ends 14p, 14d with an inner lumen extending therethrough. The particular length of the dilator 14 can vary, but the dilator 14 typically has a length that is greater than that of the outer sheath 12 such that the dilator 14 can extend through the outer sheath 12 with a distal end 14d of the dilator 14 extending from the distal end 12d of the outer sheath 12 and into the body cavity. At the same time, the proximal end 14p of the dilator 14 and the handle 20 should likewise extend from the proximal end 12p of the outer sheath 12, as explained below. The diameter of the dilator 14 can also vary, but typically the dilator 14 has a diameter such that the dilator 14 can be inserted into the inner lumen of the outer sheath 12, and that the inner lumen of the dilator is configured to receive a variety of instruments and/or other devices therethrough, including but not limited to the guidewire 16. For example, the dilator 14 can have an inner diameter of approximately 4 mm to 8 mm. The diameter of the dilator 14, particularly at the distal end 14d, can also increase proximally along the length thereof to facilitate dilation of the tissue as the dilator 14 is pushed therethrough. The diameter of the dilator 14 should be sufficient to dilate the tissue such that, after the removal of the dilator 14 from the outer sheath 12, there remains a sufficient working channel through the tissue if needed.

The dilator 14 also includes a handle 20 that can be removably coupled thereto such that the handle 20 can be removed from the dilator 14 and/or the dilator 14 and the handle 20 can then be removed from the inner lumen of the outer sheath 12 after insertion through and dilation of the tissue. The handle 20 can be removably mated to the dilator 14 in a variety of ways. For example, the handle 20 can include one or more tabs 22 extending distally from a distal end 20d of the handle 20 that are configured to mate to one or more corresponding recesses (not shown) formed on a proximal end 14p of the dilator 14. Any number of tabs 22 can be formed on the handle 20 to mate to any corresponding number of recesses in the dilator 14. A person skilled in the art will appreciate, however, that the handle 20 can mate to the dilator 14 using any technique that allows the handle 20 to be detached from the dilator 14, or the handle 20 can be unitary with the dilator 14. The tabs 22 of the handle 20 can also abut corresponding recesses formed in the outer sheath 14 such that the handle 20 of the dilator 14 can rest securely against the outer sheath 14 to allow for increases stability during insertion of the guidewire insertion device 10 through tissue. The handle 20 can also have a variety of configurations, but in the illustrated embodiment the handle 20 has a generally bulbous shape. A person skilled in the art will appreciate, however, that the handle 20 can have any size and shape that facilitates a user comfortably and effectively gripping the handle 20 and pushing the outer sheath 12 and the dilator 14 through tissue. In one exemplary embodiment, the handle 20 can include other features that facilitate locking and unlocking the guidewire 16 with respect to the dilator 14. For example, the handle 20 can include a bore 24 formed therein for receiving a locking mechanism 18 to lock the guidewire 16 relative to the dilator 14, as will be discussed in more detail below.

As explained above, the guidewire 16 can be inserted through the inner lumen of the dilator 14 and it is configured to be locked and unlocked relative to the dilator 14. The length of the guidewire 16 can vary, but the guidewire 16 typically has a length such that a distal end 16d of the guidewire 16 can extend from the distal end 14d of the dilator 14 and a proximal end 16p of the guidewire 16 extends from a proximal end of the handle 20 of the dilator 14. The distal end 16d of the guidewire 16 can extend from the distal end 14d of the dilator 14 by any distance that is appropriate for a surgical procedure. By way of example, the guidewire 16 can extend from the distal end 14d of the dilator 14 by a distance in the range of 1 mm to 250 mm. The guidewire 16 can also include bone-engaging features to facilitate anchoring the guidewire 16 in bone. In the illustrated embodiment, the bone-engaging features are in the form of threads 30 formed on a distal portion of the guidewire 16. As the guidewire insertion device 10 is inserted into the body and is positioned adjacent to bone, the threads 30 on the guidewire 16 can be used to anchor the tip of the guidewire 16 into the bone. A person skilled in the art will appreciate that the guidewire 16 can have a variety of other features for anchoring the guidewire 16 in bone, including but not limited to any other types of protrusions or extensions extending from the guidewire 16.

A variety of techniques can be used to lock and unlock the guidewire 16 relative to the dilator 14. In one exemplary embodiment, a locking member is provided that is configured to slide over the guidewire 16 and removably couple to the dilator 14 to selectively lock and unlock the position of the guidewire 16 relative to the dilator 14. In the illustrated embodiment, the locking member is in the form of a locking bolt 18 that has a generally elongate cylindrical shape with a lumen extending therethrough along its longitudinal axis. The inner lumen of the locking bolt 18 can have any diameter as long as it is has a diameter sufficient to receive the guidewire 16, enabling the guidewire to slide therethrough. The locking bolt 18 has a proximal end 18p that includes a cylindrical planar surface with a diameter greater than a distal end 18d of the locking bolt 18. The distal end 18d of the locking bolt 18 includes threads formed on at least a portion of the outer surface of the distal end 18d. A person skilled in art will appreciate that the threads can be formed on all or a portion of the locking bolt as long as the threads are formed at least on a distal end thereof. The threads of the locking bolt 18 are configured to mate with corresponding threads formed on the inner surface of the lumen of the handle 20 of dilator 14 to cause the distal end 18d of the locking bolt 18 to compress and lock the guidewire 16 within the lumen of locking bolt 18 relative to the dilator 14.

Figure 9:
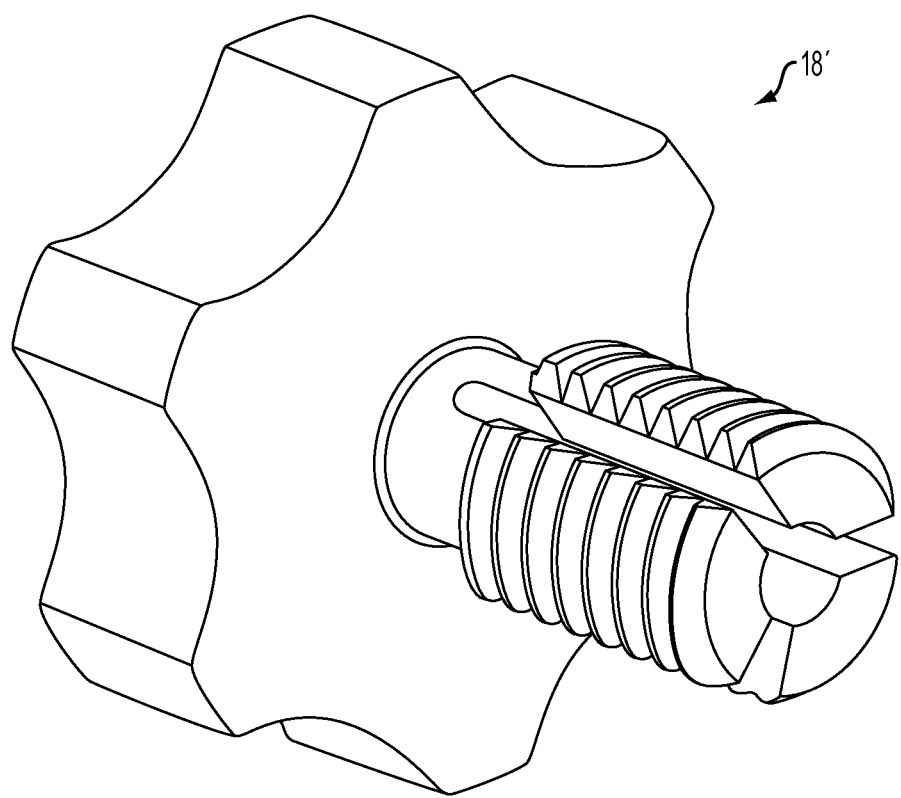
FIG. 9 is a perspective view of one embodiment of the locking mechanism of FIG. 1.

The distal end 18d of the locking bolt 18 can be configured to be compressed in a variety of ways, but in the illustrated embodiment the distal end 18d of the locking bolt 18 includes a compressible lumen formed therein, which decreases in diameter when the locking bolt 18 is in the locked position. As such the lumen of the locking bolt 18 engages and locks the guidewire 16 relative to the dilator 14. In particular, the distal end 18d of the locking bolt 18 includes at least one slit 32 formed therein and it is configured to allow the locking bolt 18 to compress to lock the guidewire 16 relative to the dilator 14. A person skilled in the art will appreciate that the locking bolt 18 can include any number of slits formed therein to allow the locking bolt 18 to compress. For example, the locking bolt 18' shown in FIG. 9 includes first, second, and third slits formed in the distal end of the locking bolt 18'.

Figure 6:
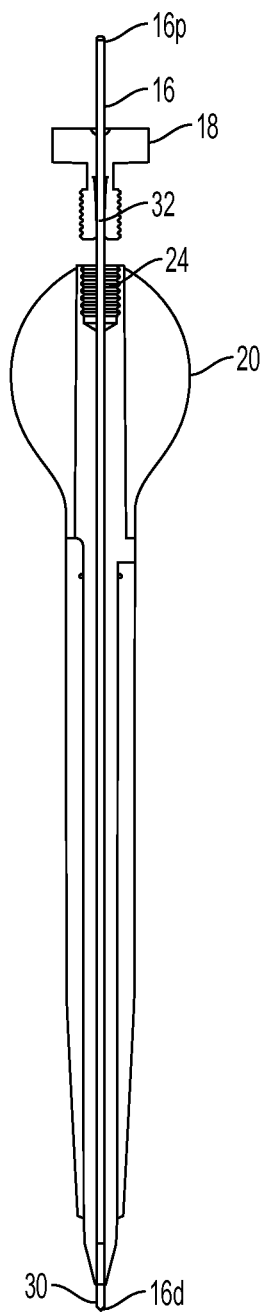
FIG. 6 is a cross-sectional side view of the guidewire insertion device of FIG. 5.
Figure 7:
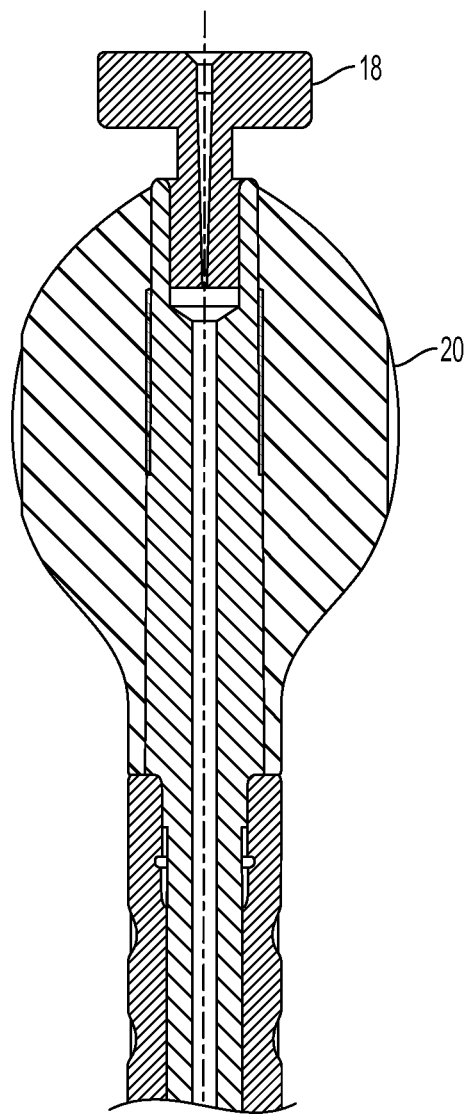
FIG. 7 is a cross-sectional side view of a proximal end of the guidewire insertion device of FIG. 1 showing the locking mechanism removably mated to a handle of the dilator.
Figure 8:
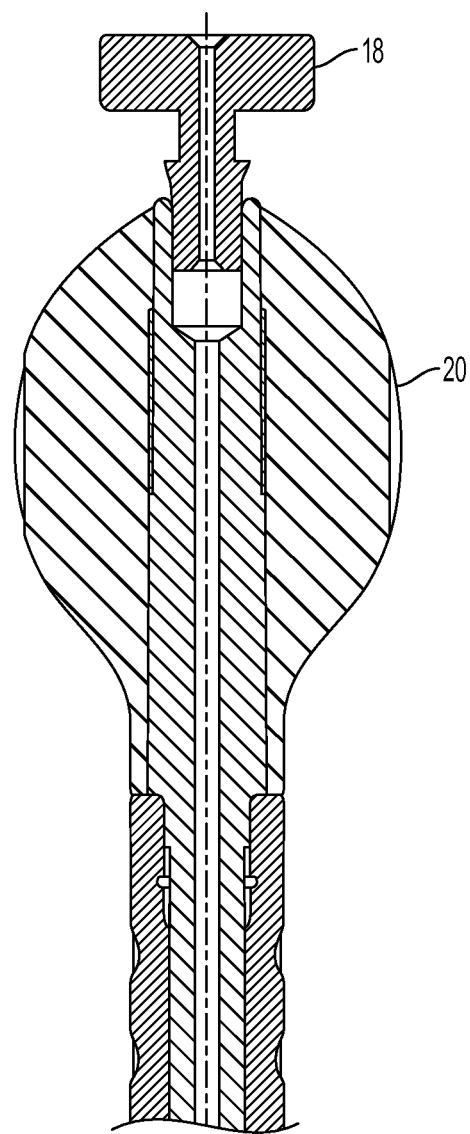
FIG. 8 is a cross-sectional side view of the proximal end of the guidewire insertion device of FIG. 1 showing the locking mechanism partially mated to the handle of the dilator.

In addition to one or more slits being formed in the distal end 18d of the locking bolt 18, the bore 24 of the handle 20 is tapered such that its diameter decreases from its proximal end to its distal end. As shown in FIG. 6, the lumen within the distal end 18d of the locking bolt 18 is compressed as the threads on the distal end 18d of the locking bolt 18 mate with the corresponding threads formed in the bore 24. As the locking bolt 18 is advanced through the bore 24, the diameter of the distal end 18d of the locking bolt 18 decreases and the lumen of the locking bolt is compressed due to the tapered shape of the bore 24. As a result, the distal end 18d of the locking bolt 18 engages the guidewire 16, clamping down on the it to lock the position of the guidewire 16 relative to the dilator 14 and keep the guidewire 16 stationary.

In another exemplary embodiment, the bore formed in the handle can have a constant diameter, and the outer surface of the distal end of the locking bolt can be tapered such that the diameter of the locking bolt can increase proximally. When the locking bolt is mated to the bore in the handle of the dilator, the lumen within the locking bolt is constricted and the guidewire locked in position relative to the dilator.

Figure 10:
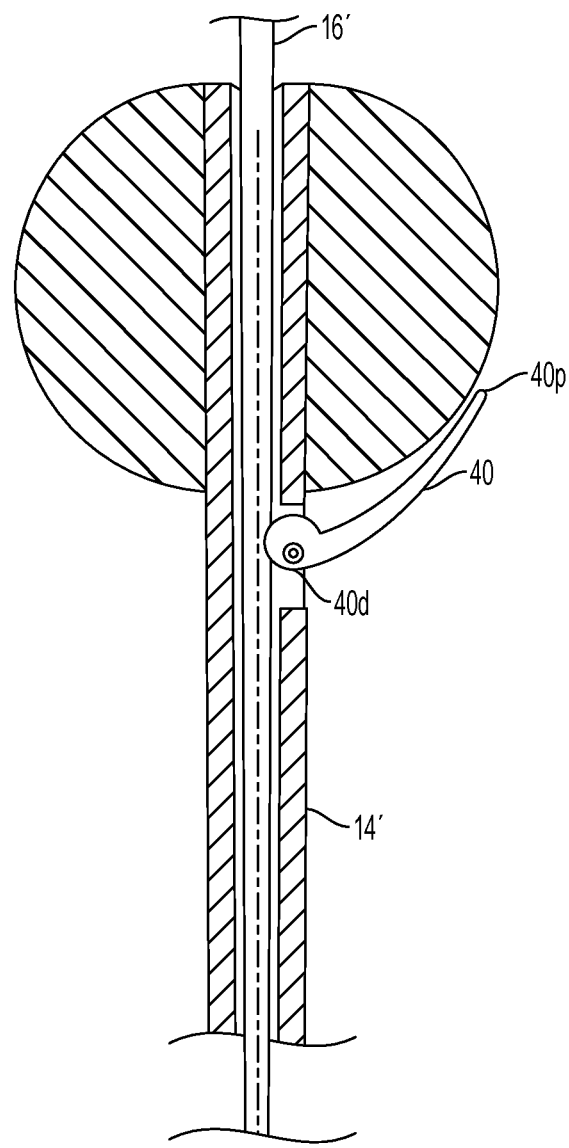
FIG. 10 is a side view of another exemplary embodiment of a guidewire insertion device having a locking mechanism pivotally coupled to a dilator and showing the locking mechanism in a locked position.
Figure 11:
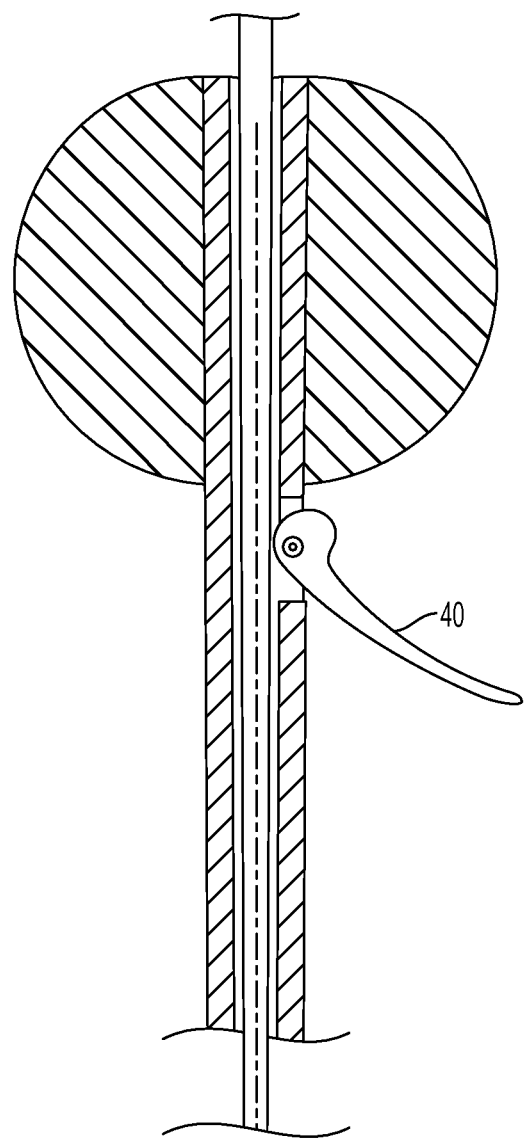
FIG. 11 is a side of the guidewire insertion device of FIG. 9 showing the locking mechanism in an unlocked position.

In another exemplary embodiment, the locking mechanism is in the form of an elongate member 40, shown in FIGS. 10-11, that is configured to pivot to selectively lock and unlock the guidewire 16' relative to the dilator 14'. The elongate member 40 has a distal end 40d that is pivotally coupled to the dilator 14' such that pivotal movement of the elongate member 40 can apply a force to the guidewire 16' to lock the guidewire 16' relative to the dilator 14'. The elongate member 40 can have any size and shape to allow a user to pivot the elongate member 40 as long as the elongate member 40 is long enough to extend through an opening formed in the dilator 14' and contact the guidewire 16' in the locked position. In one embodiment, a wall of the dilator 14' has an opening formed therein such that the distal end 40d of the elongate member 40 is pivotally coupled to an inner surface of the wall of the dilator 14'. While the elongate member 40 can have a variety of shapes and sizes, the distal end 40d of the elongate member 40 can be shaped and positioned such that the distal end 40d of the elongate member 40 remains outside the inner lumen of the dilator 14' and separated from the guidewire 16' in the unlocked position, and the distal end 40d of the elongate member 40 is positioned inside the inner lumen of the dilator 14' and against the guidewire 16' in the locked position. The distal end 40d of the elongate member 40 can lock the guidewire 16' relative to the dilator 14' in a number of ways. For example, the distal end 40d of the elongate member 40 can apply force to the guidewire 16' and push the guidewire 16' against the wall of the inner lumen of the dilator 14' such that the guidewire 16' remains stationary relative to the dilator 14'. In another example, the distal end 40d of the elongate member 40 can include surface features that can engage the guidewire 16' and prevent the guidewire 16' from sliding through the inner lumen of the dilator 14' and keep it locked relative to the dilator 14'.

Figure 12:
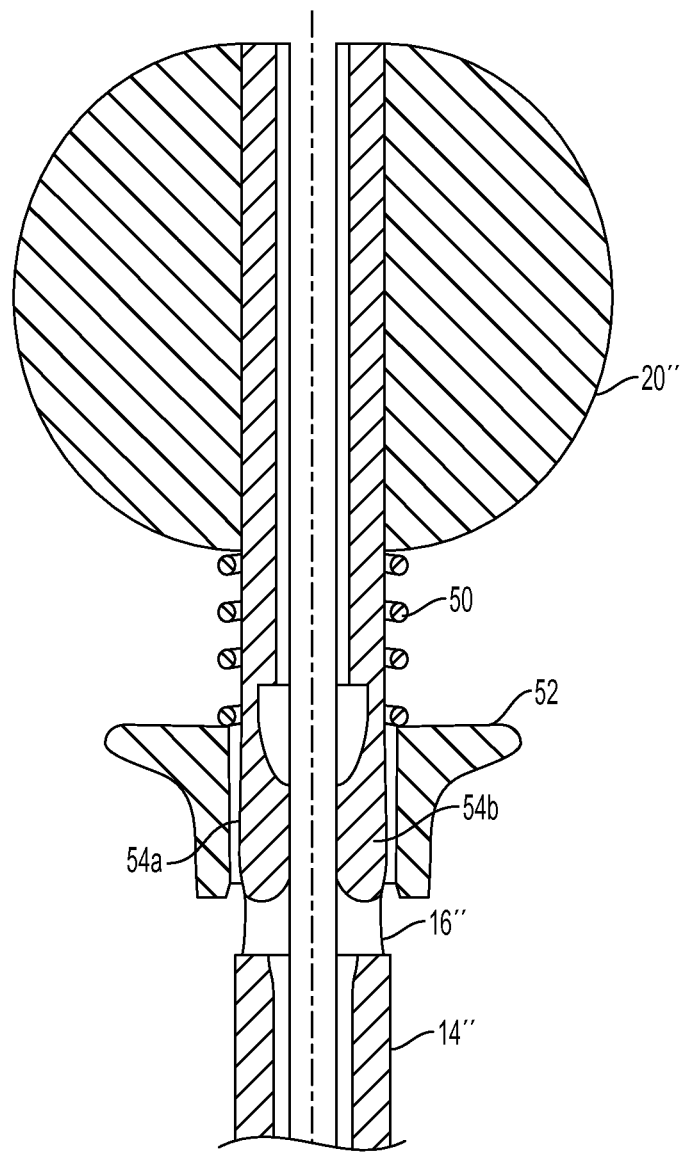
FIG. 12 is a side view of yet another exemplary embodiment of a guidewire insertion device having a locking mechanism in the form of a spring and showing the locking mechanism in a locked position.
Figure 13:
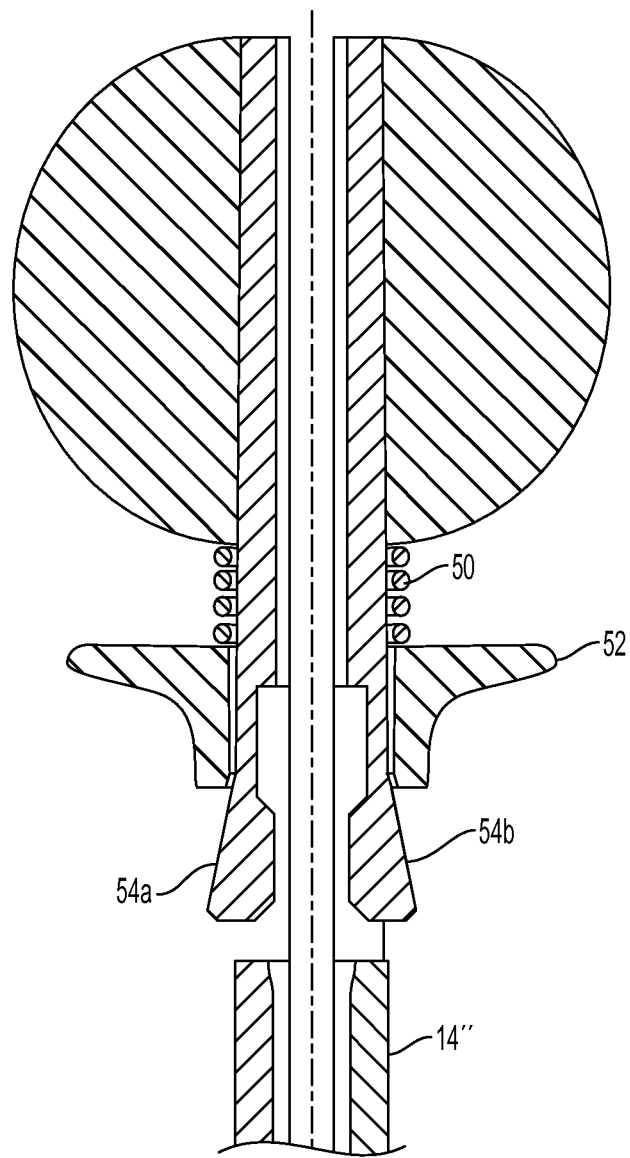
FIG. 13 is a side view of the guidewire insertion device of FIG. 11 showing the locking mechanism in an unlocked position such that the spring is compressed due to a manual force on the spring.

In yet another exemplary embodiment, the locking mechanism is in the form of a biasing element that is configured to bias a guidewire in the locked position such that the guidewire 16" is stationary relative to the dilator 14". By way of example, the biasing element can be a spring 50, as shown in FIGS. 12-13. In the embodiment shown in FIGS. 12-13, the spring 50 is disposed around a portion of the dilator 14" with its proximal end 50p applying a force to a distal end of the a handle 20" of the dilator 14", and its distal end 50d applying a force to a proximal end of a collar 52 disposed around the dilator 14". The collar 52 has a generally cylindrical shape with an opening extending therethrough such that the collar 52 can slide along the dilator 14" and move between a distal position in which the collar 52 is biased distally by the spring 50 and the guidewire 16" is locked, and proximal position in which the collar 52 is moved manually in a proximal direction to overcome the force of the spring 50 to unlock the guidewire 16". In the illustrated embodiment, the collar 52 has a proximal end that includes a flange with a diameter greater than a distal end of the collar 52, providing a surface for a user to manually move the collar 52 in a proximal direction. As explained below, the collar 52 is effective to move first and second arms 54a, 54b into and out of engagement with the guidewire 16" to lock and unlock the guidewire 16" relative to the dilator 14". The arms 54a, 54b can have a variety of configurations, but in the illustrated embodiment the arms 54a, 54b are in the form of extensions that extend from a portion of the dilator 14". The arms 54a, 54b are movable such that the arms 54a, 54b can engage and compress the guidewire 16" when the collar 52 is in the distal position in which it is positioned over the arms 54a, 54b, locking the guidewire 16" relative to the dilator 14". The arms 54a, 54b thus disengage from the guidewire 16" when the collar 52 is moved proximally to its proximal position, unlocking the guidewire 16" relative to the dilator 14".

In the locked position, which is the normal state as shown in FIG. 12, the spring 50 applies a force to the collar 52 such that the collar 52 is moved into its distal position in which the collar 52 is position around the first and second arms 54a, 54b. This causes the arms 54a, 54b to be moved into engagement with the guidewire 16", thus locking the guidewire 16" relative to the dilator 14". To separate the arms 54a, 54b from the guidewire 16" and unlock the guidewire 16", the biasing force of the spring 50 on the collar 52 can be overcome by moving the collar 52 in the proximal direction, for example, by a user manually manipulating the device. This allows the arms 54a, 54b to separate from the guidewire 16", thereby releasing the guidewire 16" from the dilator 14" and allowing the guidewire 16" to move relative to the dilator 14". Once the manual force applied to the collar 52 proximally is released, the spring 50 returns the collar 52 to its distal position, causing the arms 54a, 54b to move back into engagement with the guidewire 16" and thereby placing it in the locked position. A person skilled in the art will appreciate that a variety of other devices, or configurations, suitable for biasing can be used as the biasing element. A person skilled in the art will also appreciate that the spring 50 can be configured such that the spring biases the guidewire 16" in the unlocked position.

A method for inserting a guidewire into the body is also provided herein. In one embodiment, the guidewire insertion device 10 is assembled by inserting the guidewire 16 into the inner lumen of the dilator 14 such that at least a portion of the distal end 16d of the guidewire 16 extends from the distal end 14d of the dilator 14, as described above. The guidewire 16 is then locked relative to the dilator 14 using a locking mechanism such as described above. Once the guidewire 16 is so locked, the guidewire 16 will be maintained in a stationary position relative to the dilator 14. The guidewire 16 and the dilator 14 can be inserted into the inner lumen of the outer sheath 12. The distal end of the assembled device is positioned adjacent to tissue and force can be applied to the proximal end of the device, for example, the handle of the dilator 14, such that the device is pushed through the tissue and dilates the tissue to form a working channel therethrough. Once the distal end of the device reaches a desired location within the body, a force can be applied such that the guidewire is anchored inside the body, for example, into bone. The locking mechanism can then be disengaged so as to unlock the guidewire 16 relative to the dilator 14 and allow the guidewire 16 to move relative to the dilator 14. At this point, either the dilator 14 and the outer sheath 12 can be removed, leaving the guidewire 16 in place, or just the dilator 14 can be removed, leaving the guidewire 16 in place and the outer sheath 12 forming a working channel through the tissue.

One skilled in the art will appreciate that a variety of techniques can be used to further anchor the guidewire into bone after the dilator 14 has been removed.

In certain exemplary applications, the implants and instruments described herein are designed to be used in a minimally invasive surgical procedure; thus the dimensions are such that they can be inserted through a portal with an inner diameter of approximately 5 to 30 mm, more preferably 15-20 mm. This is particularly important when the implants are being used to correct a cosmetic deformity, where lengthy incisions would negate the positive cosmetic effect of the correction.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A guidewire insertion device, comprising:
    an outer sheath having an outer surface and an inner lumen extending therethrough;
    a dilator having an inner lumen extending therethrough and being configured to be removably disposable within the outer sheath;
    a guidewire configured to extend through the inner lumen of the dilator such that the guidewire is removably and replaceably disposable within the dilator; and
    a collar slidably disposed around the dilator and movable between at least a locked position in which the guidewire is locked to the dilator such that the guidewire is not movable relative to the dilator and an unlocked position in which the guidewire is movable relative to the dilator;
    wherein the dilator includes first and second arms which are movable such that the arms engage the guidewire when the collar is in the locked position and such that the arms do not engage the guidewire when the collar is in the unlocked position.

2. The device of claim 1, wherein the collar is biased to the locked position.

3. The device of claim 1,
wherein the dilator includes a longitudinal axis; and
wherein sliding the collar relative to the dilator in a first axial direction along the longitudinal axis of the dilator is effective to move the collar towards the locked position and sliding the collar relative to the dilator in a second opposite axial direction along the longitudinal axis of the dilator is effective to move the collar towards the unlocked position.

4. The device of claim 1, wherein the collar is generally cylindrical and includes an opening formed therein through which the dilator is received.

5. The device of claim 1, wherein the collar includes a proximal flange portion that has a diameter greater than a diameter of a distal portion of the collar.

6. The device of claim 1, wherein the collar is positioned around the first and second arms when the collar is in the locked position.

7. The device of claim 1, wherein the guidewire is configured to protrude from a distal end of the dilator.

8. The device of claim 7, wherein the guidewire protrudes from the distal end of the dilator by a distance of 1 mm to 250 mm.

9. The device of claim 1, wherein the guidewire includes bone-engaging features formed on a distal portion thereof.

10. The device of claim 9, wherein the bone-engaging features are in the form of threads formed on the distal portion of the guidewire.

11. A guidewire insertion device, comprising:
an outer sheath having an outer surface and an inner lumen extending therethrough;
a dilator having an inner lumen extending therethrough and being configured to be removably disposable within the outer sheath;
a guidewire configured to extend through the inner lumen of the dilator such that the guidewire is removably and replaceable disposable within the dilator:
a collar slidably disposed around the dilator and movable between at least a locked position in which the guidewire is locked to the dilator such that the guidewire is not movable relative to the dilator and an unlocked position in which the guidewire is movable relative to the dilator and
a biasing element disposed between the collar and a handle portion of the dilator and configured to bias the collar distally away from the handle portion of the dilator.

12. The device of claim 11, wherein the biasing element comprises a spring.

13. A method for inserting a guidewire into bone, comprising:
advancing a dilator through tissue to dilate the tissue, the dilator being removably disposed within an outer sheath and having a guidewire extending through an inner lumen of the dilator such that the guidewire protrudes from a distal end of the dilator and the guidewire is locked and stationary relative to the dilator;
sliding a collar with respect to the dilator to unlock the guidewire from the dilator such that the guidewire is movable relative to the dilator, the collar being disposed around the dilator; and
removing the dilator from the outer sheath while maintaining the guidewire and outer sheath in position to provide a working channel through the outer sheath.

14. The method of claim 13, further comprising anchoring the guidewire to bone.

15. The method of claim 14, wherein anchoring the guidewire to bone comprises applying force to a proximal end of the guidewire when a distal end of the guidewire is adjacent to bone.

16. The method of claim 13, wherein sliding the collar comprises pulling the collar proximally to allow first and second arms of the dilator to disengage the guidewire.

17. The method of claim 13, wherein sliding the collar comprises grasping a proximal flange portion of the dilator and sliding the collar along an exterior of the dilator against the bias of a spring.

18. A guidewire insertion device, comprising:
an outer sheath having an outer surface and an inner lumen extending therethrough;
a dilator having an inner lumen extending therethrough and having a length greater than a length of the outer sheath and being configured to be removably disposable within the outer sheath such that a distal portion of the dilator is configured to protrude from a distal end of the outer sheath and a proximal handle portion of the dilator is configured to protrude from a proximal end of the outer sheath when the dilator is disposed in the outer sheath;
a guidewire configured to extend through the inner lumen of the dilator such that the guidewire is removably and replaceably disposable within the dilator; and
a locking member that is positionable with respect to the dilator to engage first and second arms of the dilator to lock the guidewire relative to the dilator and positionable with respect to the dilator to disengage the first and second arms of the dilator to unlock the guidewire from the dilator.

* * * * *